United States Patent
Johns et al.

(10) Patent No.: US 6,214,620 B1
(45) Date of Patent: Apr. 10, 2001

(54) INDUCIBLE GENETIC SUPPRESSION OF CELLULAR EXCITABILITY

(75) Inventors: David C. Johns, Elkridge; Eduardo Marban, Lutherville, both of MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/407,945

(22) Filed: Sep. 29, 1999

Related U.S. Application Data (60) Provisional application No. 60/102,140, filed on Sep. 29, 1998.

(51) Int. Cl.[7] ............................ C12N 15/85; C12N 15/63; C12N 5/00; C07H 21/04
(52) U.S. Cl. ...................... 435/455; 435/320.1; 435/325; 536/23.1; 536/23.5; 536/24.1
(58) Field of Search ................................ 435/320.1, 455, 435/325; 536/23.1, 23.5, 24.1

(56) References Cited

PUBLICATIONS

Wang et al., J. Neurosci. 17: 882–890, The seizure locus encodes the Drosophila homolog of the HERG potassium channel, Feb. 1997.*

Zhao et al., J. Neurosci. 15: 1406–1418, Functional expression of Shaker K+ channles in cultured Drosophila "Giant" neurons derived from Sh cDNA transformants: distinct properties, distribution, and turnover, Feb. 1995.*

Yang et al., Proc. Natl. Acad. Sci. 87: 9568–9572, In vivo and in vitro gene transfer to mammalian somatic cells by particle bombardment, Dec. 1990.*

Gossen et al., Trends Biochem. Sci. 18: 471–475, Control of gene activity in higher eukaryotic cells by prokaryotic regulatory elements, Dec. 1993.*

Wang et al., Human Gene Therapy 7: 1743–1756, Construction of human factor IX expression vectors in retroviral vector frames optimized for muscle cells, Sep. 1996.*

Blomer et al., J. Virology 71: 6641–6649, Highly efficient and sustained gene transfer in adult neurons with a lentivirus vector, Sep. 1997.*

Lachmann et al., Mol. Medicine Today 3: 404–411, The use of herpes simplex virus–based vectors for gene delivery to the nervous system, Sep. 1997.*

Han et al. "Expression of noninactivating K+ channels(aK5.1) into Aplysia neuron using heat–shock inducible promoters and the study of its effect on neuronal activities" Fourth Meeting of the Asian–Pacific Society for Neurochemistry and the Annual Meeting of the Korean Society for Neuroscience; Seoul, Korea; Jun. 24–26, 1998, vol. 70, No. Suppl. 2, p. S20.

No et al. "Ecdysone–Inducible Expression in Mammalian Cells and Transgenic Mice" Proceedings of the National Academy of Sciences, USA, vol. 93, 1996, pp. 3346–3351.

(List continued on next page.)

Primary Examiner—Robert A. Schwartzman
Assistant Examiner—Katharine F Davis
(74) Attorney, Agent, or Firm—Banner & Witcoff, Ltd.

(57) ABSTRACT

Graded, reversible suppression of cellular excitability represents a logical goal of therapy for epilepsy and intractable pain, as well as for cardiac arrhythmias. To achieve such suppression, "electrical silencing" genes are transferred into cells with sensitive control of transgene expression. For example, an ecdysone-inducible promoter drives the expression of inwardly rectifying potassium channels in polycistronic adenoviral vectors. While normal electrical activity is not affected, after the induction of gene expression excitability is suppressed.

38 Claims, 10 Drawing Sheets

(1 of 10 Drawing Sheet(s) Filed in Color)

OTHER PUBLICATIONS

Nuss et al. "Reversal of potassium channel deficiency in cells from failing hearts by adenoviral gene transfer: A prototype for gene therapy for disorders of cardiac excitability and contractility." Gene Therapy 1996, vol. 3, No. 10, 1996 pp. 900–912.

Hebert "General principles of the structure of ion channels" American Journal of Medicine, Jan. 1998, vol. 104, No. 1, Jan. 1998 pp. 87–98.

Johns et al. "Suppression of neuronal and cardiac transient outward currents by viral gene transfer of dominant–negative Kv4.2 constructs" Journal of Biological Chemistry Dec. 12, 1997, vol. 272, No. 50 pp. 31598–31603.

Gingrich et al. "Inducible gene expression in the nervous system of transgenicmice" Annual Review of Neuroscience Annual Review of Neuroscience. 1998 Annual Review Inc. P.O. Box 10139, 4139 El Camino Way, Pal Alto, California 94306, vol. 21, 1998, pp. 377–405.

Johns et al. "Inducible genetic suppression of neuronal excitability" Journal of Neuroscience Mar. 1, 1999, vol. 19, No. 5, Mar. 1, 1999, pp. 1691–1697.

* cited by examiner

INDUCIBLE GENETIC SUPPRESSION OF CELLULAR EXCITABILITY

This application claims the benefit of provisional application Ser. No. 60/102,140, filed Sep. 29, 1998.

This invention was made using funding supplied by the U.S. National Institutes of Health. Under the terms of NIH grant DA-00266, the U.S. government retains certain rights in the invention.

TECHNICAL FIELD OF THE INVENTION

This invention is related to the field of cellular excitability. In particular it is related to the disorders in cellular excitability which lead to epilepsy, cardiac arrhythmias, and intractable pain.

BACKGROUND OF THE INVENTION

Excessive cellular excitability underlies a variety of common, often lethal diseases, ranging from epilepsy to cardiac ventricular arrhythmias. Conventional therapeutic efforts to suppress excitability in such disorders center around pharmacological block of selected ion channels, mechanical disruption of an irritable focus, or devices such as pacemakers or defibrillators. Drug block of ion channels, while sometimes effective, is plagued by side effects attributable to the systemic administration of drugs needed only in small areas of the body. Mechanical disruption of epileptic or arrhythmic foci is traumatic, irreversible and often ineffective. Implantable devices designed to terminate hyperexcitation are expensive, and are activated only after the seizure has begun. Thus there is a need in the art for additional means of treating hyperexcitability which are more effective, less invasive, and less expensive.

SUMMARY OF THE INVENTION

It is an object of the present invention to provide methods for altering the excitability of cells.

It is another object of the present invention to provide methods for altering the excitability of cells, such as those involved in epilepsy, cardiac arrhythmia, and intractable pain.

These and other objects of the invention are achieved by providing a method of altering cellular excitability. A genetic construct is delivered to a cell. The genetic construct comprises an inducible promoter and a sequence encoding an ion channel. The inducible promoter regulates transcription of the sequence. The inducible promoter is regulated by an externally controllable stimulus. Thus, the excitability of the cell is regulated by the externally controllable stimulus.

According to another embodiment of the invention, a method is provided for altering cellular excitability. A genetic construct is delivered to a neuronal cell. The genetic construct comprises an ecdysone-inducible promoter and a sequence encoding a potassium ion channel. The inducible promoter regulates transcription of the sequence. The inducible promoter is regulated by muristerone A and similar ligands such as ponasterone. Thus, the excitability of the neuronal cell is regulated by muristerone A.

These and other embodiments provide the art with new methods and tools for counteracting pathological hyperexcitability of cells.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 2A–FIG. 2E: Infection of SCG neurons with inducible adenovirus constructs

Confocal images of SCG neurons infected with AdEGI-Kir2.1 and AdVgRXR in the absence (FIG. 2A) and presence (FIG. 2B) of muristerone A.

FIG. 3A–FIG. 3I: Exogenous expression of Kir2.1 suppresses excitability

The effects of a supra-threshold stimulus on a control cell do not change with the addition of barium (FIG. 3A, FIG. 3B). The membrane current recorded from the same cell under these conditions using a ramp protocol from −138 mV to +22 mV over 500 ms (FIG. 3C). The addition of barium had little or no detectable effect on the outwardly rectifying I–V curves in control cells. The response to a sub-threshold stimulus on a Kir2.1 infected cell (FIG. 3D) is markedly changed by the addition of barium (FIG. 3E), in both panels, the arrow indicates the cessation of the applied stimulus. The I–V curve for this cell is much different upon addition of barium (FIG. 3F). Membrane current recordings from a Kir2.1 infected cell shown in normal saline (FIG. 3G), upon superfusion with saline containing barium (FIG. 3H) and upon washout (FIG. 3I).

FIG. 4A–FIG. 4B: Cumulative effects of exogenous expression of Kir2.1

Cells expressing Kir2.1 are hyperpolarized with respect to control cells. This effect is reversed upon blocking the Kir2.1 channels (FIG. 4A). Increasing amounts of Kir2.1 current increase the size of the stimulus needed to fire an action potential (FIG. 4B).

DETAILED DESCRIPTION

It is a discovery of the present inventors that inducible genetic suppression can be used as an alternative approach to the treatment and prevention of hyperexcitability. For example, overexpression of inwardly rectifying potassium channel genes driven by an inducible promoter inhibits evoked and spontaneous activity in cultured neurons. Blocking the expressed channels reverses the suppression of excitability. Thus, induction of exogenous hyperpolarizing genes effectively suppresses excitability. The inducible expression of such genes represents a new therapeutic principle for use in disorders of hyperexcitability, and provides a powerful research tool for probing the contributions of specific regions of the nervous system to the global functional response. Similarly, such inducible expression can be used in vitro or in vivo to screen for and identify new agents for enhancing or decreasing excitability or the suppression of excitability.

Broadly, the invention utilizes gene transfer of ion channels under the control of an inducible promoter to cells, tissues or organs to alter their electrical properties. Any gene delivery vector or vehicle can be used, so long as efficient gene transfer to cells occurs. Thus viral or non-viral vectors can be used. Similarly, naked DNA, DNA-coated particles, liposome encapsulated DNA, poly-lysine complexed DNA all can be used in the practice of the invention. Viral vectors which can be used include adenovirus, both partially and completely deleted, adeno-associated (AAV) vectors, herpes (HSV) vectors, both partially and completely deleted, and retro-viral vectors including lentiviral vectors. For a review of these vectors see Robbins et al., 1998, Trends Biotechnol 16, 35–40.

Any mode of delivery can be used, so long as effective gene transfer is accomplished to the desired target cells. Thus delivery can be accomplished to cells in vitro, or alternatively delivery may be intramuscular, subcutaneous, intravascular, intrathecal, intravenous, etc. Catheters may be used to deliver the constructs of the invention to the desired location. These include magnetically-localizable catheters and injection catheters.

Inducible promoters which may be used in performing the methods of the present invention include those regulated by hormones and hormone analogs such as progesterone, ecdysone and glucocorticoids as well as promoters which are regulated by tetracycline, heat shock, heavy metal ions, interferon, and lactose operon activating compounds. For review of these systems see Gingrich and Roder, 1998, *Annu Rev Neurosci* 21, 377–405. When using non-mammalian induction systems, both an inducible promoter and a gene encoding the receptor protein for the inducing ligand are employed. The receptor protein typically binds to the inducing ligand and then directly or indirectly activates transcription at the inducible promoter.

Ion channels which can be used in the practice of the present invention include all proteins, natural and synthetic, which allow ionic currents to flow across a lipid bilayer membrane. These include proteins which are found in the plasma membrane as well as in intracellular and mitochondrial membranes. The proteins may be in their native form or may have been altered by molecular genetics to make them fit a specific need (i.e., altering the activation or inactivation properties or altering the protein so that it acts as a dominant-negative suppressor as demonstrated in Johns et al, 1999, *J Neurosci* 19, 1691–7; Johns et al., 1995, *J Clin Invest* 96,1152–8; Johns et al., 1997, *J Biol Chem* 272, 31598–31603; Nuss et al., 1999, *J Clin Invest* 103,889–96; Nuss et al., 1996, *Gene Ther* 3, 900–912.) Suitable ion channels include, but are not limited to, potassium channels, including voltage gated, ligand gated and inwardly rectifying channels; sodium channels including voltage gated and ligand gated; calcium channels including voltage gated and ligand gated; chloride channels including voltage gated and ligand gated; non-specific cation channels; non-specific anion channels; and neurotransmitter-gated ion channels, e.g., glutamate receptors.

Any tissue or cell which contains excitable membranes can be targeted by the method of the invention. Such tissues and cells include neuronal, muscle (cardiac, skeletal and smooth), and endocrine tissues and cells. In addition other tissues may be targeted in which altering the electrical properties creates a desired phenotype, such as cancerous tissue. The elicited effects include increasing or decreasing excitability as measured by electrical activity, secretory activity, contractile function, metabolic rate and growth status.

The method of the invention has benefit for treating a wide variety of diseases and pathological states. These include: heart failure, cardiac arrhythmias, endocrine disorders such as pituitary adenomata, epilepsy, intractable pain, skeletal muscle disorders including dystrophies, myotonia and ALS, heritable disorders of ion channels (long QT syndrome, heritable atrial fibrillation, cystic fibrosis, and others), hypertension, cancer, and Alzheimer's disease.

According to one preferred mode of the operation, inducible constructs according to the invention are delivered to intact hearts. By this method, one can increase or decrease refractoriness of the heart, increase or decrease the speed of conduction, increase or decrease focal automaticity, and/or alter the spatial pattern of excitation.

Thus the invention can achieve modification of the sinus node and/or surrounding atrial tissue. This can be used to eliminate inappropriate sinus tachycardia, e.g., by introducing potassium channel genes to decrease nodal excitability. Introduction of inducible ion channel genes into focal areas of the heart can be used to create regions of automaticity. This is useful for indications such as sick sinus syndrome, Stokes-Adams attacks, syncope, chronic fatigue syndrome, and cardiomyopathies (hypertrophic and dilated). Introduction of HCN genes and/or calcium channel subunits can increase local automaticity and/or induce pacemaker activity where it is not normally present.

Introduction of inducible ion channel genes can also be used to slow and/or block conduction. For example, this can be achieved by overexpression of K channels, decrease of sodium or calcium channel activity (e.g., by decoy beta subunits), or manipulation of cell-cell communication (e.g., by dominant-negative or nonfunctional connexins). In the AV node, one can achieve modification of atrioventricular conduction velocity and/or pattern, e.g., to control ventricular rate in atrial fibrillation, or to modify conduction in AV nodal reentrant tachycardia. In the tricuspid annulus, one can induce bidirectional block and prevent atrial flutter. In the atrium, one can induce lines of conduction block or slowing to terminate or to prevent atrial fibrillation (e.g., a genetic "maze" procedure). In the ventricle, one can induce bundle-branch block as a means of achieving discoordinate activation, e.g., in hypertrophic cardiomyopathy.

In order to achieve modification of repolarization, widespread rather than focal delivery is preferred. This is achievable by overexpression or functional knockout of K channels (e.g., by dominant-negative constructs), or by alteration of sodium or calcium channel activity (e.g., by decoy beta subunits). In the ventricle one can use such treatments for treatment of long QT syndrome (acquired or hereditary), heart failure, or Brugada syndrome. In the atrium, one can use such treatments for treatment and prophylaxis of atrial fibrillation.

Neuronal excitability can be modified genetically in an inducible and reversible fashion. The ecdysone regulatory system, one of many possible inducible transcription systems which can be used, has little background activity when appropriate amounts of receptor virus are used and yet is inducible to high levels. Under the conditions described below, there was an inherently high level of variability of expression amongst infected cells. This was the result of co-infecting with less than saturating amounts of both the therapeutic virus and the receptor virus. FIG. 1B shows that increasing the number of the receptor viruses per cell, while holding the number of test viruses constant, increases the amount of expression. Similar experiments varying the number of test viruses delivered while holding the number of receptor virus constant showed that this also affected expression levels. The variable levels of GFP fluorescence visible in infected cells confirmed these predictions. For these reasons we did not perform dose response experiments in neurons, where the level of muristerone A was also varied. According to one embodiment of the invention, the hormone receptor complex genes can be included on the same vector as the inducible gene construct, optionally under the control of a tissue-specific promoter, to accomplish more uniform tissue-specific expression. The use of the internal ribosome entry site (IRES) was quite beneficial in allowing easy detection of positive cells without having to increase the amount of ion channel expression to levels which are not physiologically relevant. These properties enabled us to examine a wide range of electrophysiological effects.

On one end, low levels of expression of Kir2.1 sufficed to inhibit spontaneous activity (FIGS. 3G–I) despite a relatively modest 66% increase in the current needed to reach threshold. At the other extreme, two cells, which were not included in the analysis, exhibited $Ba^{2+}$-sensitive currents >1.5 nA. In these two cells, action potentials could not be elicited when a maximal current stimulus (2 nA) was applied for up to 50 ms; nevertheless, in the presence of $Ba^{2+}$ both of these neurons fired action potentials with modest stimuli. Such stimulus currents far exceed the probable summed inputs for any single neuron and thus represent a complete silencing of electrical activity.

The higher infection efficiency of the glial cell population (100%) vs the neuronal population (52%) has been previously observed by us as well as others. This represents another potential limitation of this system, in that there may indeed be profound effects of hyperpolarizing the supporting cell population. To avoid this complication in-vivo, several strategies are employed. These include the use of neuronal-specific promoters, of vectors modified to increase neuronal tropism, or of vectors which are naturally more neurotropic.

The potential applications for this technology are widespread. The role of ion channels in nervous system development has previously been explored by the use of blocking reagents. The current methods enable genetic manipulation of excitability at different points in development and potentially in specific regions of the CNS. From a clinical standpoint, this targeted and controllable delivery of ion channels form the basis for new treatments of diseases of excitability such as epilepsy. In addition, targeted delivery of these (or similar) vectors results in controllable suppression of excitability with the potential for genetic analgesia in the treatment of intractable pain. The ability to turn gene expression on and off at will enables the titration of responses while preserving remarkable safety; should therapy prove detrimental or ineffective in a particular patient, the inducing agent can simply be withdrawn.

EXAMPLES

Materials and Methods used in the Examples

Plasmid Vectors

The coding sequence for the human Kir2.1 gene was amplified using the polymerase chain reaction to allow in frame fusion to EGFP in the vector pEGFP-C3 (Clontech, Palo Alto, Calif.) creating pEGFP-Kir2.1. Kir2.1 was also cloned into the vector pGFP-IRES to create the vector pGFP-IRES-Kir2.1. The adenovirus shuttle vector pAdLox was modified to replace the CMV promoter with the ecdysone inducible promoter from pIND-1 (Invitrogen, San Diego, Calif.) making the vector pAdEcd. The expression cassettes from pGFP-IRES, pGFP-IRES-Kir2.1 and pEGFP-Kir2.1 were cloned into the multiple cloning site of pAdEcd making the vectors pAdEGI, pAdEGI-Kir2.1 and pAdEG-Kir2.1. The plasmid, pAdVgRXR, was made by cloning the expression cassettes from pVgRXR (Invitrogen, San Diego, Calif.) into pAdLox, encodes the ecdysone receptor.

Cell Culture

A549, 293 and CRE8 cells (CCL-185, CRL 1573, American Type Culture Collection, Rockville, Md. and respectively) were grown in DMEM (CellGro, Mediatech, Washington D.C.) supplemented with 10% fetal bovine serum (FBS), 2 mM Glutamax, 1X Penicillin-Streptomycin, and 15 mM HEPES, pH 7.4 (LifeTechnologies, Gaithersburg, Md.) at 37 C° in a 5% $CO_2$, humidified incubator.

Viral Vectors

Recombinant adenovirus vectors were generated by Cre-lox recombination. A 25 $cm^2$ flask (T25, Sarstedt, Newton, N.C.) of CRE8 cells was co-transfected with 2.1 (g of purified (5 viral DNA and 2.1 (g of purified shuttle vector DNA using Lipofectamine Plus (Life Techologies). Cells were incubated 5 to 9 days until cytopathic effects (CPE) were observed. Cells and media were transferred to a 50 ml polypropylene tube (Sarstedt) and freeze-thawed in a dry ice-ethanol bath and shaking 37 C° water bath. Cells and debris were removed by centrifugation in a clinical centrifuge and two ml of the supernatant was added to a 90% confluent T25 and returned to the incubator until CPEs were observed. This procedure was repeated three to four times at which time the virus was analyzed for purity by plaque assays. Viruses were then expanded and large-scale virus purifications were performed as previously described. Virus titers were determined by plaque assays and particle numbers were determined by absorbance at 260 nm on a DU640 spectrophotometer (Beckman Instruments, Fullerton, Calif.). As has previously been reported, the particle number exceeded the infective particle number by between 40 and 100 fold. Multiplicities of infections were calculated based on the number of plaque forming units per ml.

Neuronal Cultures

SCG neurons were prepared by enzymatic dissociation from ganglia taken from newborn rat pups. Neurons were plated onto glass coverslips coated with rat tail collagen. Neurons were grown in DMEM/F12 containing 10% FBS and treated with 10 (M cytosine arabinoside starting 24 hours after plating. Culture media contained (–nerve growth factor at 100 ng/ml (Boehringer Mannheim, Indianapolis, Ind. or kindly supplied by Dr. David Ginty, JHUMS, Baltimore, Md.).

Infections

Cells (A549 or primary SCG neurons) were infected by replacing their normal growth media with DMEM with 2% FBS and the appropriate amount of virus for 2–4. The amount of virus used for A549 cells was varied as described for each experiment, while the amount of virus used for SCG neurons was held constant at ~50 moi of the test virus and 5 moi of the receptor virus. Infection medium was then replaced with normal growth medium. Expression was induced by addition of muristerone A (1 (M in FIG. 1B and 3 $\mu$M in all other experiments; Invitrogen) for twenty-two (A549 cells) or 48 (SCG neurons) hours before assays were performed. The dose of muristerone A was selected to maximally activate the receptor based on previously reported dose-response curves (No et al), which agreed with our own preliminary dose-response curves (not shown).

Immunohistochemistry-Infected SCG neurons were fixed and stained as previously described.

Confocal Microscopy

Images were taken on a laser scanning confocal microscope (PCM 2000, Nikon Inc., Melville, N.Y., EX 488, EM 505–530) with a 60x objective lens (NA 1.2).

Electrophysiology

Experiments were performed at 21–23° C. Whole-cell currents were recorded with Axopatch 1-D amplifier (Axon Instruments, Foster City, Calif.) sampled at 10 kHz and filtered at 1–5 kHz. The pipette solution contained (in mM) 140 K-Glutamate, 1 $MgCl_2$, 4 EGTA, 4 MgATP, 10 HEPES (pH 7.2). The bath solution for neurons contained (in mM) 140 NaCl, 5.4 KCl, 2 $CaCl_2$, 1 $MgCl_2$, 10 glucose, 10 HEPES (pH7.4); for A549 cells 140 KCl was substituted for NaCl.

Statistics

Pooled data are shown as means (the standard error of the mean (s.e.). Data was analyzed using two-factor ANOVA. Between group comparisons were made post hoc with the Fisher's least-significant-difference test.

Flow Cytometry

Single color flow cytometry was used to determine the mean fluorescence intensity of infected A549 cells. Cells were induced one day after infection, twenty-two hours later, cells were trypsinized, washed and re-suspended in 0.5 ml of PBS. Cells were analyzed on a FacStar (Becton Dickinson) using forward and side scatter gates to exclude dead cells and cell fragments and collecting $1 \times 10^4$ events per sample.

Example 1

Inducible viral constructs

Figure 1A:
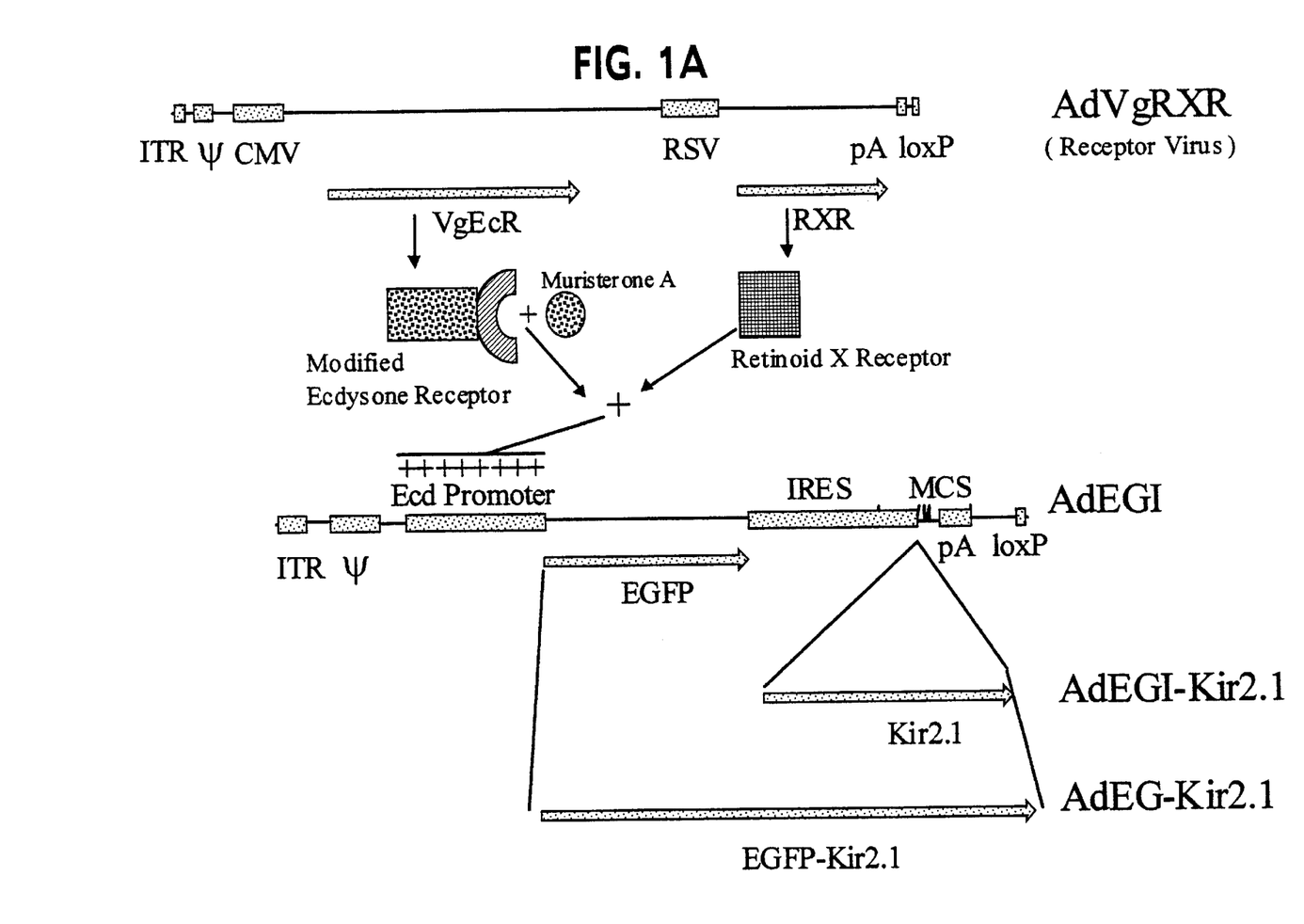
FIG. 1A–FIG. 1D Ecdysone inducible adenovirus constructs allow tight control of gene expression Schematic representation of the basis for the ecdysone inducible adenovirus vectors; VgECR—modified ecdysone receptor, RXR—retinoid X receptor, ITR—inverted terminal repeat, ψ—packaging signal, ECD promoter—ecdysone-inducible promoter, IRES—internal ribosome entry site, pA—SV40 poly-adenylation signal, MCS—multiple cloning site (FIG. 1A). Infection of A549 cells with variable multiplicities of infection (moi's) of both an adenovirus containing an ecdysone inducible promoter controlling expression of a cassette containing GFP, an internal ribosome entry site (IRES) and a multiple cloning site (AdEGI) and an adenovirus which expresses the modified ecdysone receptor and the retinoid X receptor (AdVgRXR) resulted in muristerone A dependent inducible expression of GFP (FIG. 1B, ■ vs ●). In the absence of AdVgRXR background expression was minimal (FIG. 1B, ▲) and such cells were entirely refractory to muristerone A (FIG. 1B, ○). Expression of GFP in A549 cells, infected with both AdVgRXR and AdEGI, can be induced with 3 μM muristerone A for the indicated amounts of time (FIG. 1C; columns 2–4), reduced to near background levels by the removal of muristerone A for 36 hours (FIG. 1C; column 5) and re-induced to the original induction level with muristerone A for 24 hours (FIG. 1C; column 6). Membrane currents from A549 cells infected with AdVgRXR and AdEGI-Kir2.1 in the absence (I=−5 pA/pF; n=2) and presence (I=−80(12 pA/pF; n=4) of 3 μM muristerone A (FIG. 1D).
Figure 1B:
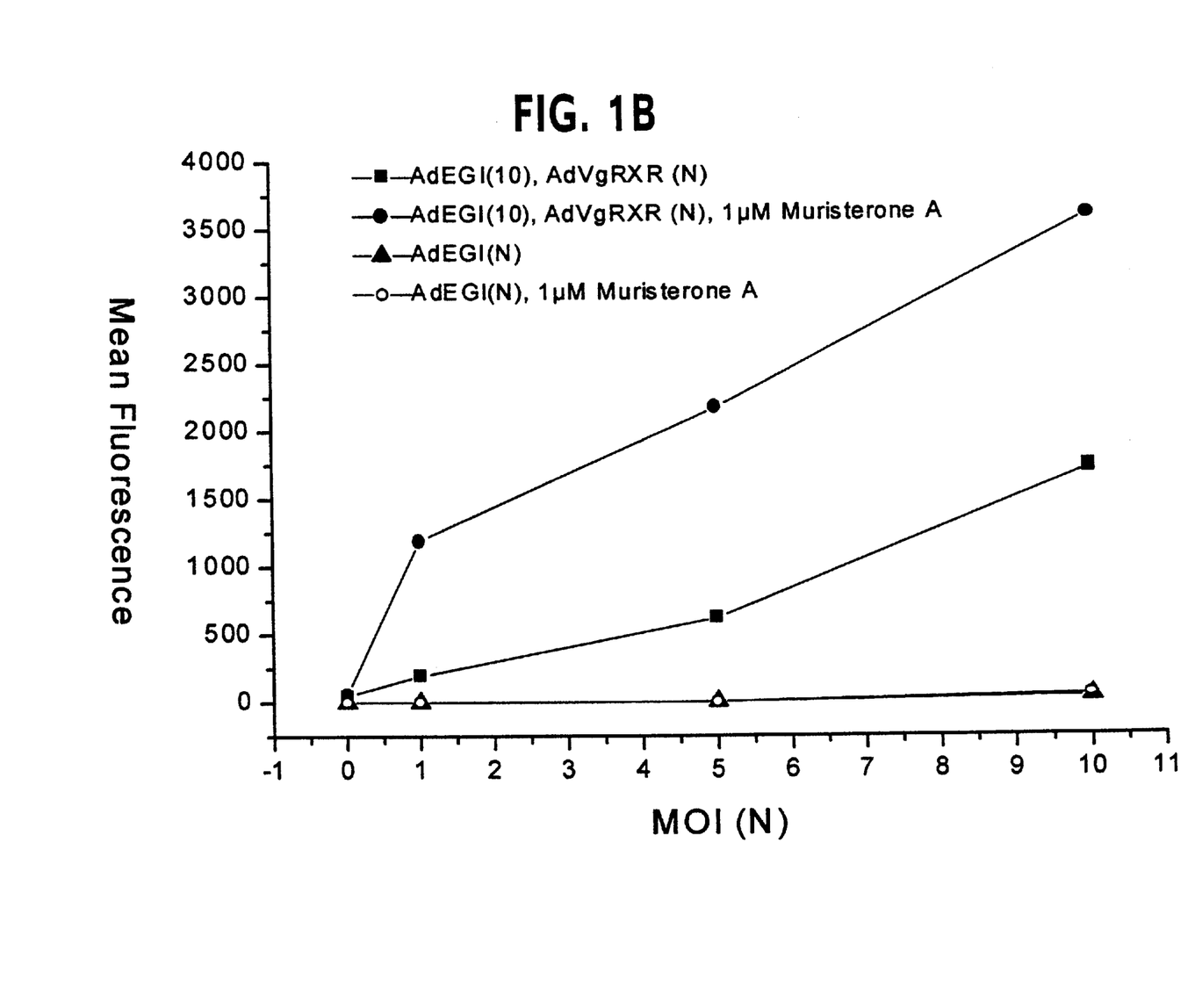
Figure 1C:
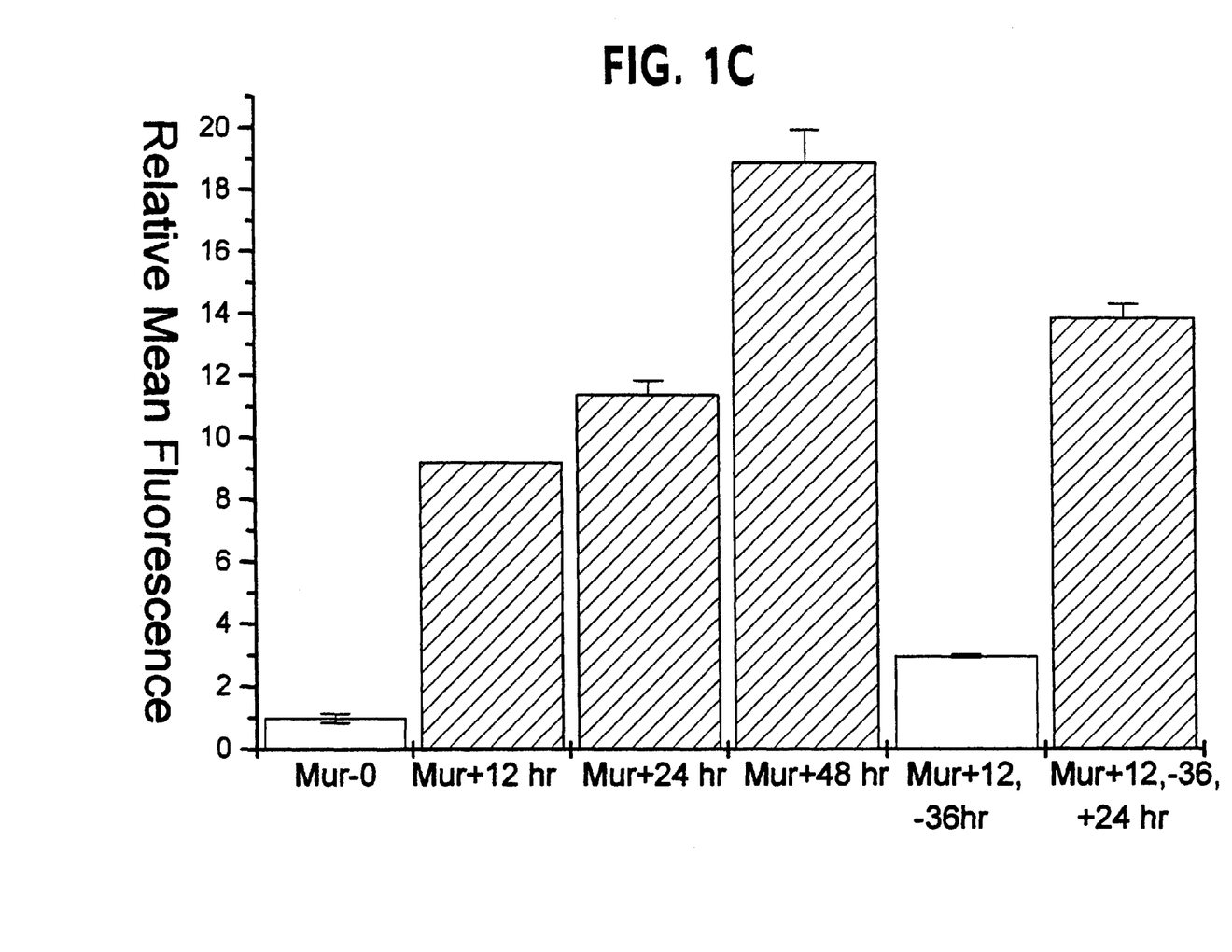
Figure 1D:
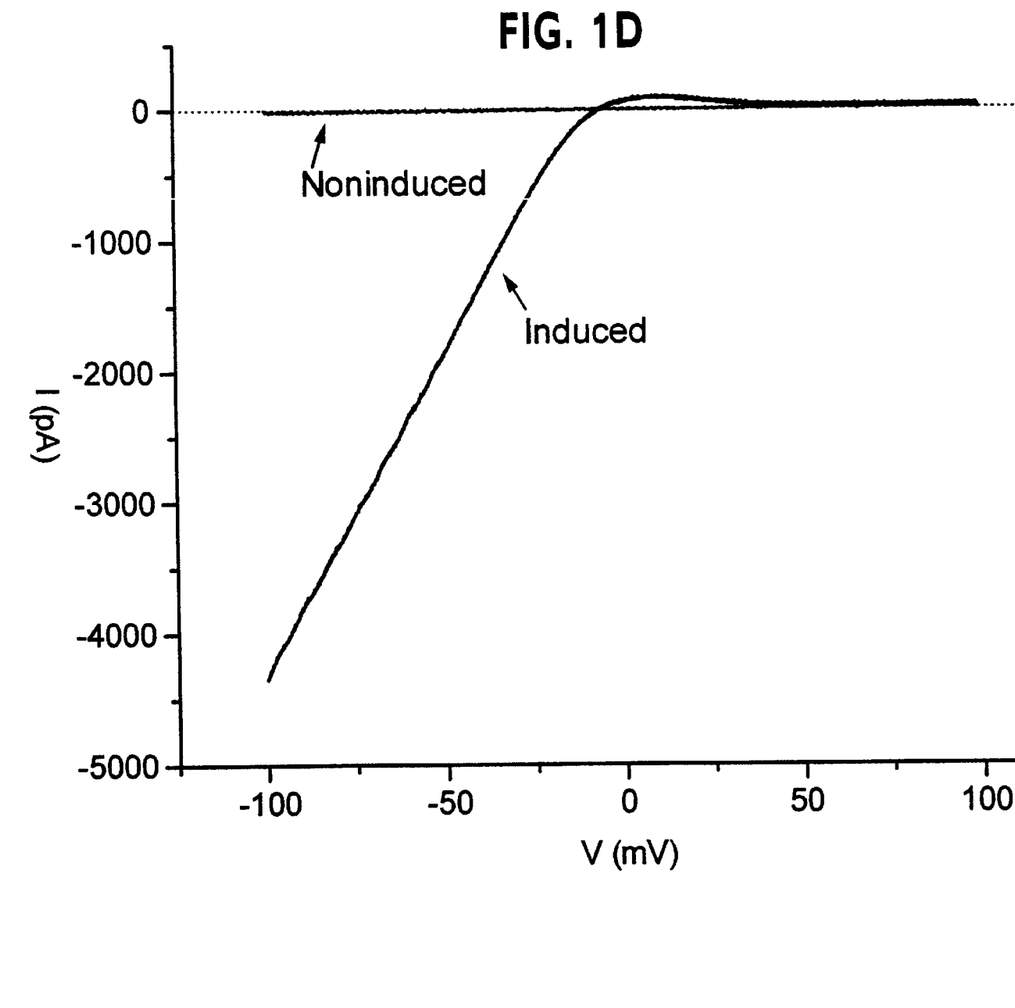

To achieve sensitive control of gene expression after somatic gene transfer, we created adenoviruses that enabled ecdysone-inducible expression of ion channels and reporter genes in mono- or polycistronic vectors (FIG. 1A). The poly-cistronic vector, as shown, results in an approximate 3:1 ratio of GFP protein to ion channel protein, allowing sensitive detection of cells without undue overexpression of the ion channel. Infection of A549 cells with a stoichiometric ratio of 10 ecdysone-driven reporter virus (AdEGI) per ecdysone/retinoid X receptor viruses (AdVgRXR) produced low basal levels of expression of green fluorescent protein (GFP), but >15-fold enhancement after addition of the ecdysone analog muristerone A (FIG. 1B). Excess levels of receptor virus lead to higher levels of basal (noninduced) expression (FIG. 1B) as well as a slight decrease in the fold induction achievable. This decrease in the level of induction may be in part due to a higher percentage of induced cells above the saturation level of the flow cytometer. The absolute level of expression was increased with increasing levels of the receptor. Removal and re-addition of muristerone A (FIG. 1C) could turn expression off and then on again. To test for inducibility with channel-containing constructs, A549 cells were co-infected with an adenovirus which expresses both GFP and Kir2.1 (AdEGI-Kir2.1; moi=5) and AdVgRXR (moi=0.5). When induced, 80–90% of the cells were GFP-positive in contrast to <1% of infected but non-induced cells (based on flow cytometry measurements; data not shown). Membrane current recordings from infected but non-induced cells showed no inwardly rectifying current, while induced cells expressing GFP exhibited robust inwardly-rectifying currents (FIG. 1D). Overexpression of such channels under physiological conditions in neurons would be predicted to hyperpolarize cells and to suppress excitability.

Example 2

Infection of neuronal cells

Figure 2A:
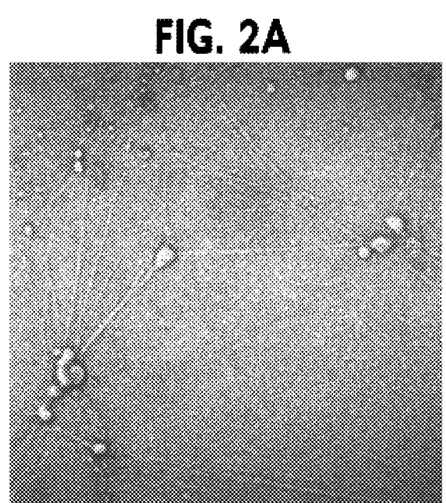
Figure 2B:
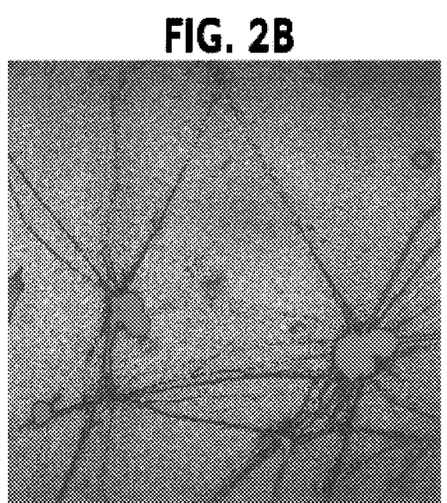
Figure 2C:
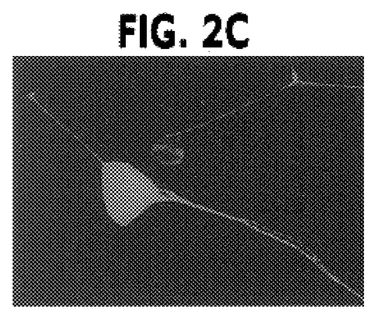
FIGS. 2C, 2D & 2E show a neuron expressing the fusion protein, EGFP-Kir2.1, following fixation and staining with a polyclonal antibody to GFP and a monoclonal antibody against the microtubule associated protein 2 (MP2). A FITC labeled goat anti-rabbit secondary antibody was used to detect the presence of GFP (FIG. 2D) and a Cy3 conjugated secondary antibody was used to detect the bound anti-MAP2 (FIG. 2C). MAP2 is normally distributed in the dendrites and cell bodies.
Figure 2D:
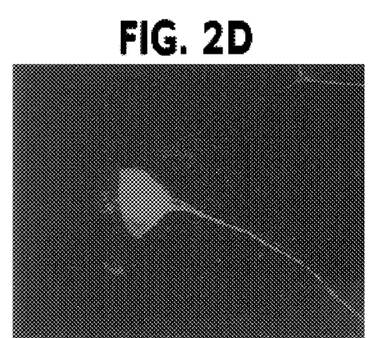
Figure 2E:
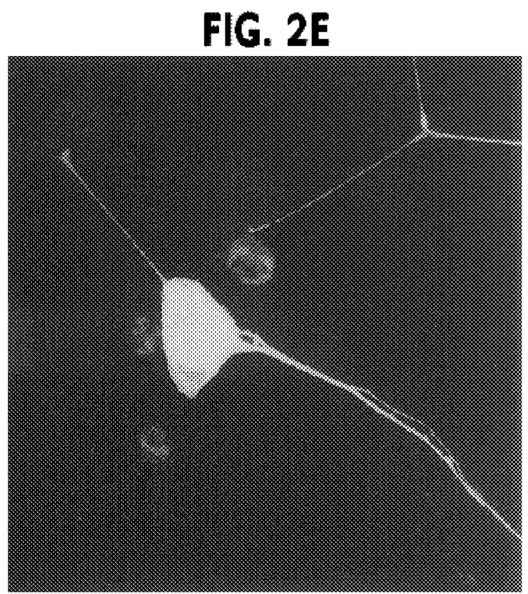

To confirm efficient infection and inducibility in excitable cells, we used neurons cultured from neonatal rat superior cervical ganglia (SCG). SCG neurons have been used extensively for studies of electrophysiology, biochemistry and development; in addition, these neurons are known to be amenable to adenoviral gene transfer. SCG neurons infected with AdEGI-Kir2.1 and AdVgRXR for 48 hours and treated with vehicle for 22 hours exhibited negligible GFP fluorescence (FIG. 2A), in contrast with cells imaged 22 hours after the addition of muristerone A (FIG. 2B). A vector containing a GFP-Kir2.1 fusion protein (AdEG-Kir2.1) enabled us to track the distribution of the expressed channel complex. Comparison of the distribution of GFP (FIG. 2D) to that of microtubule associated protein 2 (MAP2; panel 2C) showed substantial overlap (panel 2E); indeed, Kir2.1 protein was distributed throughout the surface and internal membranes of the neurons. In these experiments, 52% of the MAP-2 positive cells were also GFP positive (N=100); in addition, all of the glial cells that could be identified by visible light were GFP positive.

Example 3

Suppression of neuronal excitability

Figure 3A:
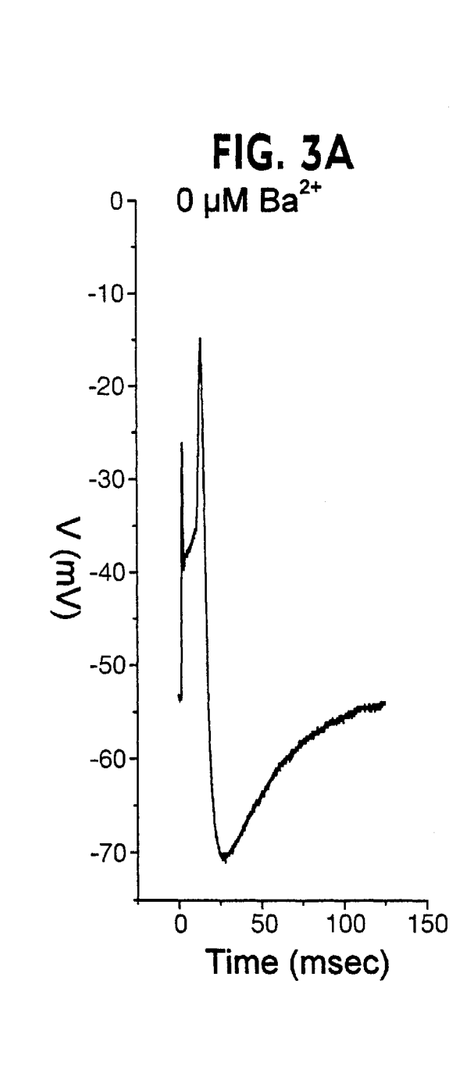
Figure 3B:
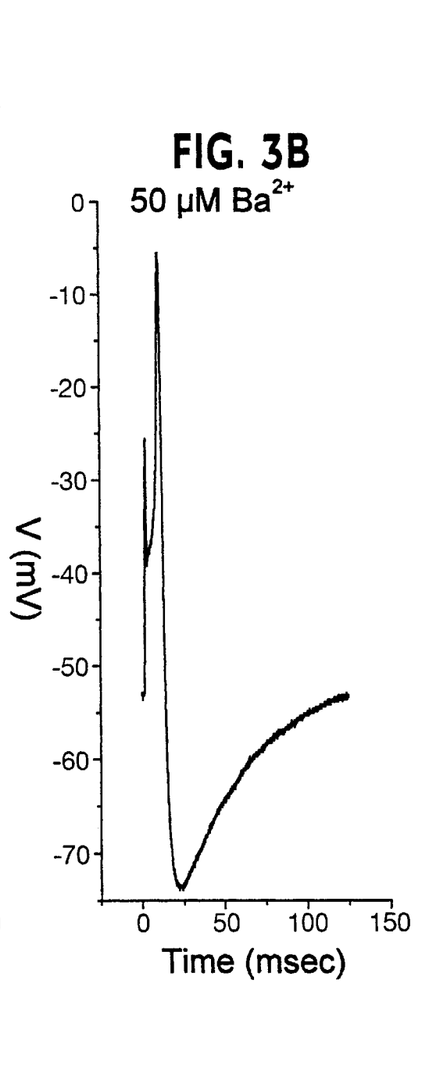
Figure 3C:
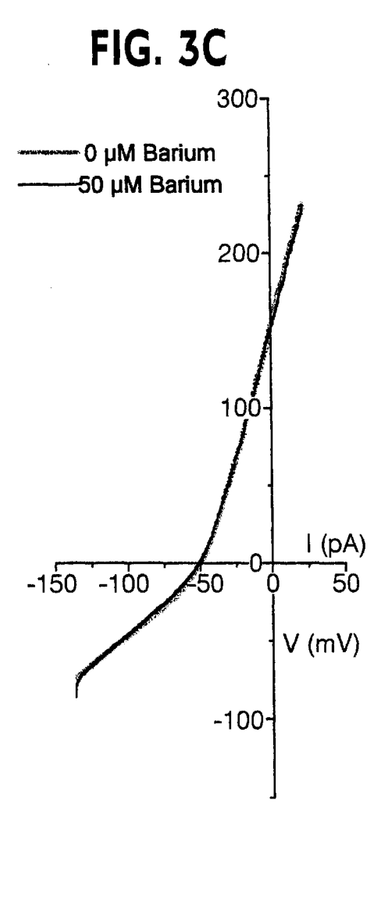
Figure 3D:
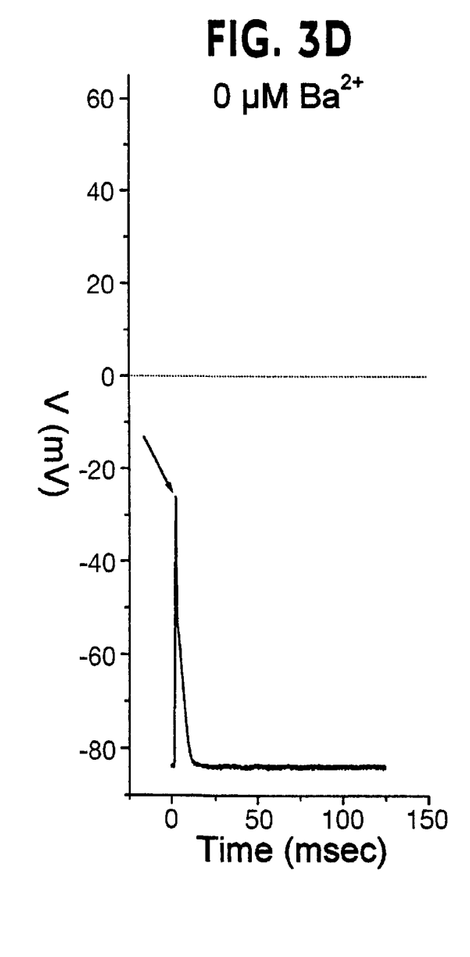
Figure 3E:
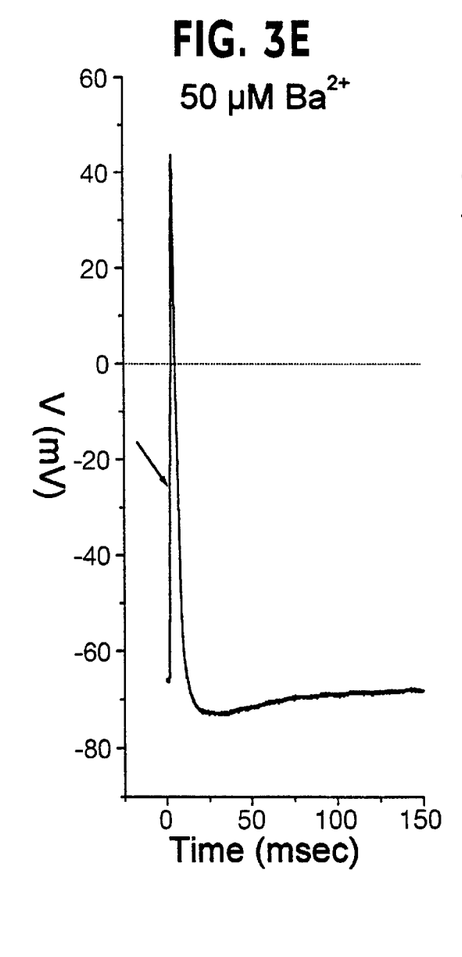
Figure 3F:
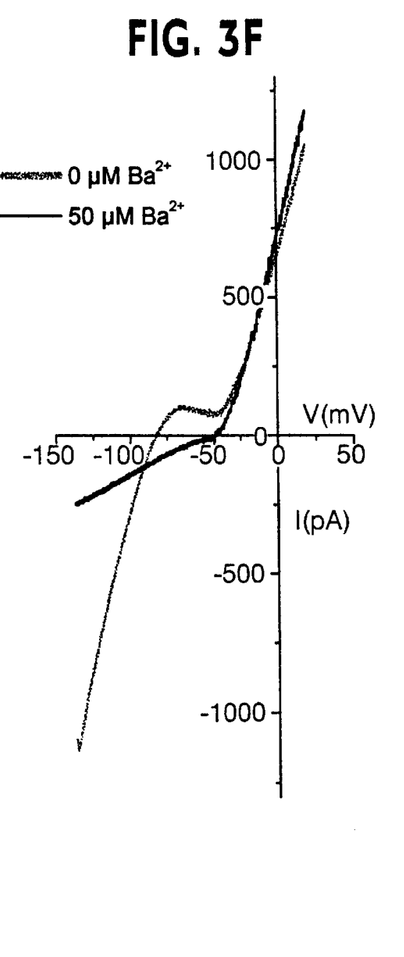
Figure 3G:
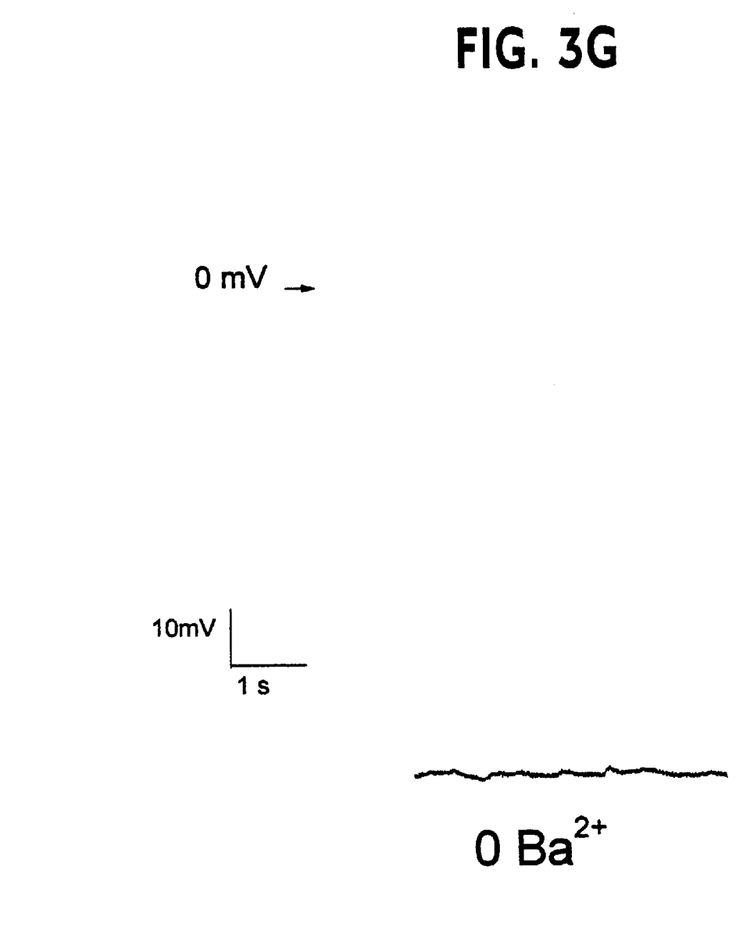
Figure 3H:
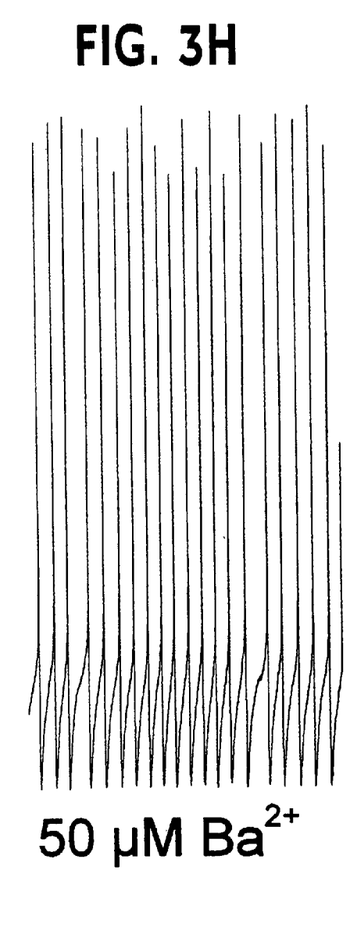
Figure 3I:
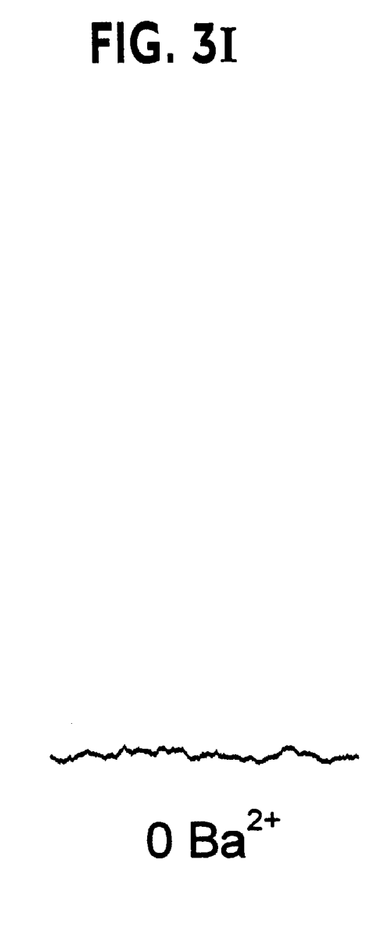

In the process of characterizing the phenotypic consequences of Kir2.1 gene transfer and induction, we first compared action potentials and membrane currents in AdEGI-infected and uninfected SCG neurons, and found no differences; data from these two groups were thus combined as "control cells" (data not shown). Barium ($Ba^{2+}$) selectively blocks inwardly rectifying potassium channels, which are relatively sparse in control SCG neurons. Stimulated action potentials in a control cell were identical in the absence and presence of $Ba^{2+}$ (FIGS. 3A,B), as were membrane currents (FIG. 3C). In contrast, neurons expressing Kir2.1 exhibited diminished excitability. Inward current injection produced only a sub-threshold depolarization in an induced cell infected with AdEGI-Kir2.1 (FIG. 3D); after the addition of 50 (M $Ba^{2+}$, the resting potential depolarized and a current stimulus of the same intensity evoked a full action potential (FIG. 3E). The current-voltage relations in this cell reveal marked inward rectification at baseline; the addition of $Ba^{2+}$ made the membrane currents indistinguishable from those in control cells (FIG. 3F). In addition to re-shaping evoked activity, induced Kir2.1 gene expression also suppressed spontaneous electrical activity (FIGS. 3G–I). Six of 14 control cells exhibited spontaneous activity in normal solution, but none of 14 induced Kir2.1-infected cells did so. Nevertheless, 5 of these 14 neurons began firing spontaneously after superfiision with 50 (M $Ba^{2+}$. The cell shown in FIGS. 3G–I expressed only 100 pA of $Ba^{2+}$-sensitive current at −120 mV, revealing that the amount of expression needed to achieve biologically relevant suppression was small. On the other hand, cells with as much as 1.1 nA of current also exhibited $Ba^{2+}$-induced spontaneous activity, indicating that high-level expression did not irreversibly inhibit the ability of the neuron to respond to normal synaptic input.

Figure 4A:
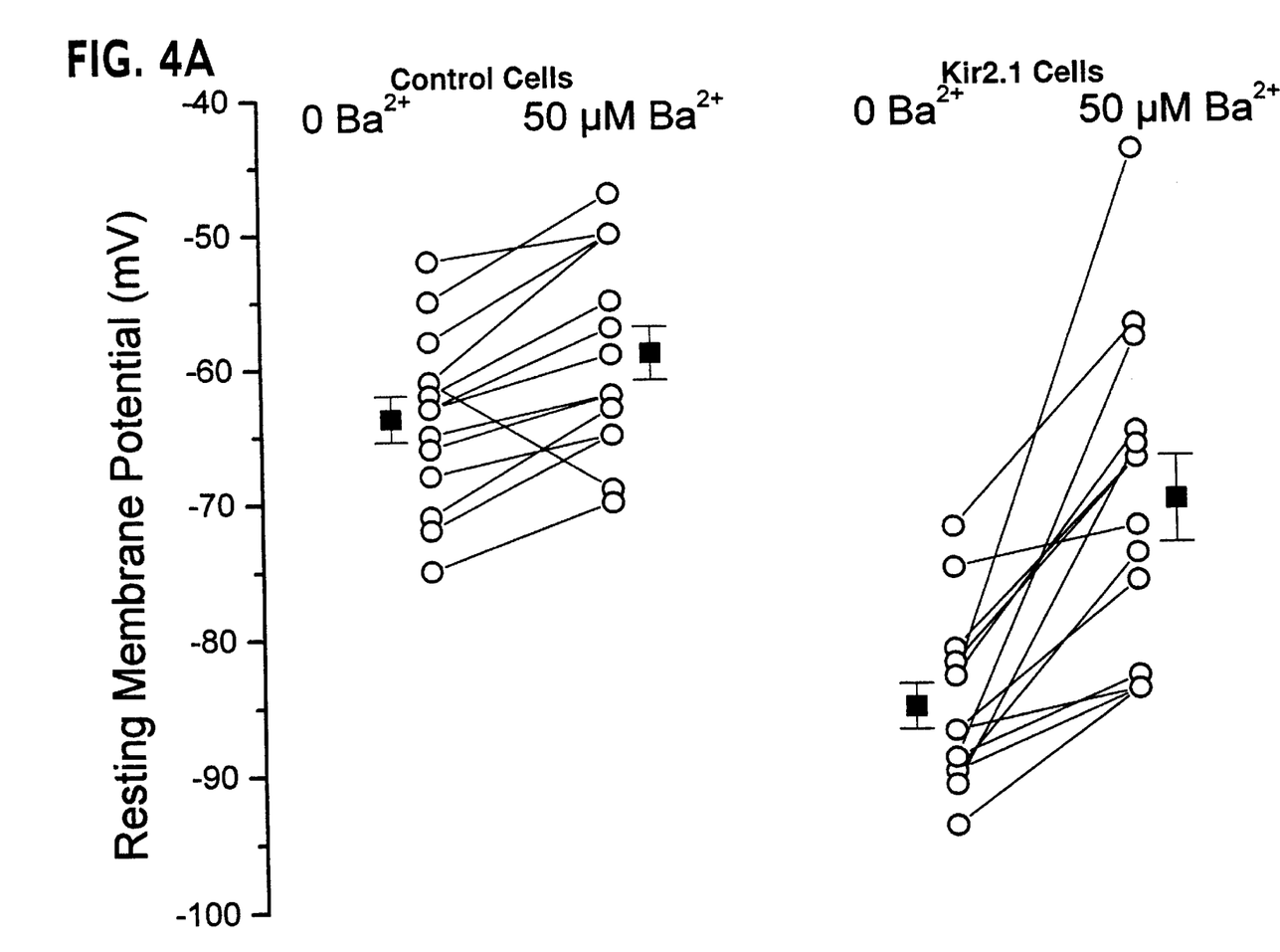
Figure 4B:
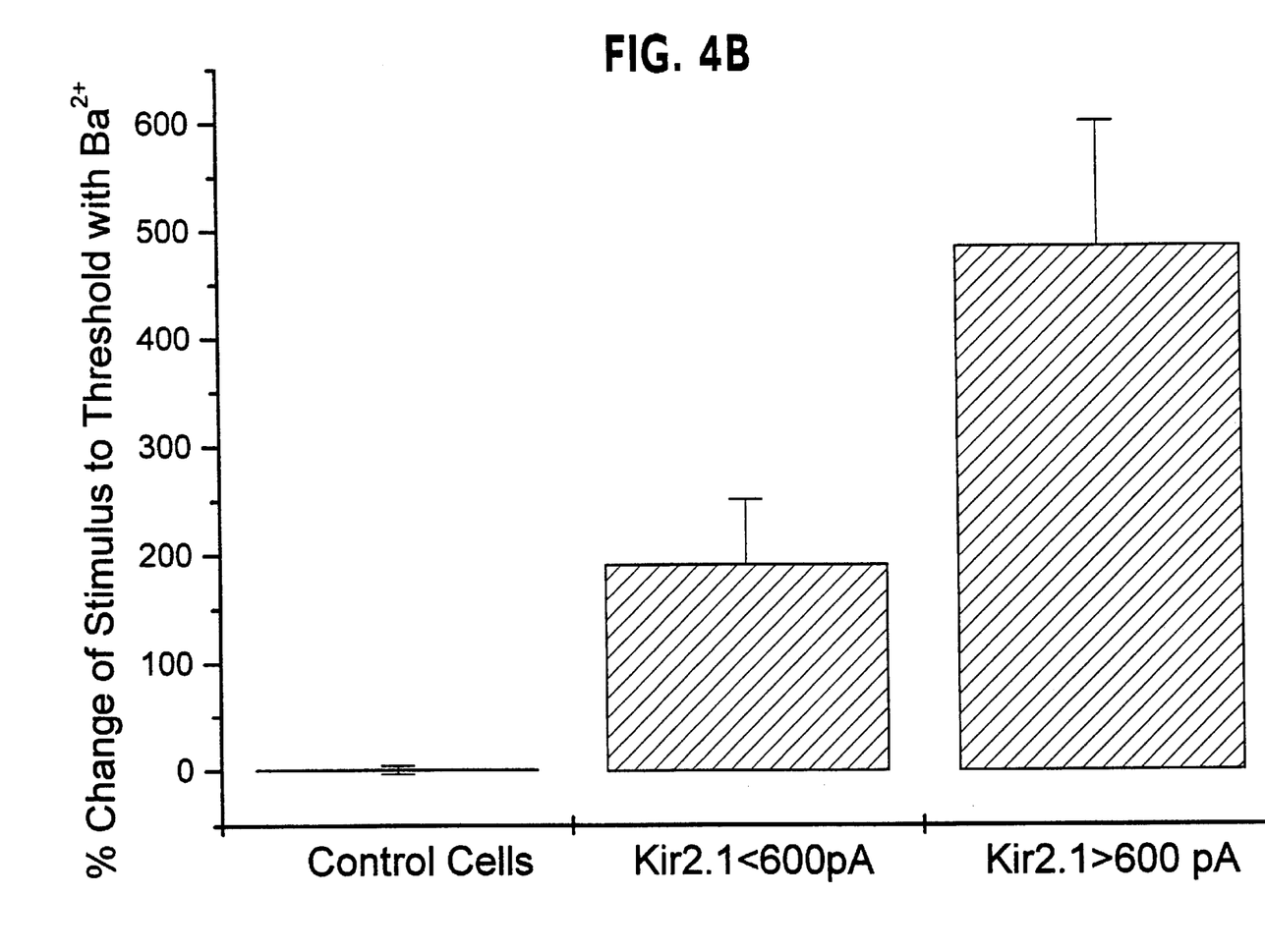

FIG. 4 summarizes the changes in resting membrane potential (panel A) and stimulus threshold (B) effected by induction of Kir2.1 expression. In the absence of $Ba^{2+}$, control cells were depolarized relative to Kir2.1-induced cells (−63 vs. −85 mV, p<0.0001). Some (but not all) of the control cells exhibited a small depolarization in response to $Ba^{2+}$, due presumably to block of low-density native inward rectifiers. In contrast, every Kir2.1-induced cell depolarized upon exposure to $Ba^{2+}$ (p<0.001). FIG. 4B quantifies the change in excitability as the difference between the threshold amount of stimulus current needed to fire an action potential in the absence and presence of 50 (M $Ba^{2+}$. The stimulus threshold was $Ba^{2+}$-insensitive in control cells. In general, Kir2.1-induced cells required dramatically greater stimuli to reach threshold in the absence of $Ba^{2+}$(p<0.0005). To examine the effects of the varying densities of expressed Kir2.1, we divided the cells into two groups based on the amount of $Ba^{2+}$-sensitive current they exhibited (600 pA was the midpoint; range=100–1100 pA). The increase in stimulus threshold was distinctly greater in the cells which expressed a higher density of Kir2.1.

REFERENCES AND NOTES

1. W. Loscher, Eur J. Pharmacol 342, 1–13, 1998; P. Jallon, Epilepsia 38, S37–42, 1997; E. Marban in Molecular basis of heart disease. K. Chien et al., eds., WB Saunders, NY, 1998
2. Adenovirus constructs were created using a CRE-Lox recombination system [S. Hardy et al., J. Virol. 71 1842–1849 (1997)]. The ecdysone-inducible promoter [D. No, T. -P. Yao, R. M. Evans, Proc, Natl. Acad. Sci. USA 93, 3346–3351 (1996)] was cloned from pInd (Invitrogen, San Diego, Calif.) into pAdLox to create pAdEcd. The coding sequence for the human Kir2.1 gene was amplified using the polymerase chain reaction to allow in frame fusion to EGFP in the vector pEGFP-C3 (Clontech, Palo Alto, Calif.) creating pEGFP-Kir2.1. Kir2.1 was also cloned into the vector pGFP-IRES [D. C. Johns et al, J. Biol. Chem. 272, 31598–31603 (1997)] to create the vector pGFP-IRES-Kir2.1. The coding sequences from these two vectors and pGFP-IRES were cloned into pAdEcd and used to generate the adenoviruses AdEG-Kir2.1, AdEGI-Kir2.1, and AdEGI respectively. The dual expression cassette from pVgRXR (Invitrogen, Can Diego, CA) wa salso cloned into pAdLox and subsequently used to generate the virus AdVgRXR.
3. A549, 293 and CRE8 cells (CCL-185, CRL 1573, American Type Culture Collection, Rockville, Md. and kindly supplied by S. Hardy, respectively) were grown in DMEM (CellGro, Mediatech, Washington D.C.) supplemented with 10% fetal bovinee serum (FBS), 2 mM Glutamine, 1X Penicillin-Streptomycin, and 15 mM HEPES, pH 7.4 (Life Technologies, Gaithersburg, Md.) at 37 C° in a 5% $CO_2$, humidified incubator. Cells (A549 or primary SCG neurons) were infected by replacing their normal growth medium with DMEM with 2% FBS and the apppropriate amount of virus for 2–4 hours. Infection medium was then replaced with normal growth medium. Expression was induced by addition of muristerone A (1–4 μM; Invitrogen) twenty-two (A549 cells) or 48 (SCG neurons) hours before assays were performed.
4. D. C. Johns et al., unpulished results.
5. I=−80±12 pA/pF at −50 mV; n=4. Experiments were performed at 21–23° C. Wholecell currents were recorded with Axopatch 1-D amplifier (Axon Instruments, Foster City, Calif.) sampled at 10 kHz and filtered at 1–5 kHz. The pipette solution contained (in mM) 140 K-Glutamate, 1 $MgCl_2$, 4 EGTA, 4 MgATP, 10 HEPES (pH 7.2). The bath solution for neurons contained (in mM) 140 NaCl, 5.4 KCl, 2 $CaCl_2$, 10 glucose, 10 HEPES (pH7.4); for A549 cells 140 Kcl was substituted for NaCl.
6. SCG neurons were prepared by enzymatic dissociation from ganglia taken from newborn rat pups [K. L. Marek, R. E. Mains, J. Neurochem 52, 1807–16 (1989)]. Neurons were plated onto glass coverslips coated with rat tail collagen [Bornstein, M. B., Lab. Invest. 7, 134–137 (1958)]. Neurons were grovn in DMEM/F12 containing 10% FBS and treated with 10 μM cytosine arabinoside starting 24 hours after plating. Culture media contained β-nerve growth factor at 50 ng/ml (Boehringer Mannheim, Indianapolis, Ind. or kindly supplied by Dr. David Ginty, JHUMS, Baltimore, Md.).
7. V. Argiro, M. I. Johnson, J. Neurosci 2, 503–12 (1982); T. K. Garyantes, W. G. Regehr, J. Neurosci 12, 96–103 (1992); S. McFarlane, E. Cooper, J. Neurophysiol 67, 1291–300 (1992); J. M. Nerbonne, A. M. Gurney, J Neurosci 9, 3272–86) (1989); S. T. Lockhart, G. G. Turrigiano, S. J. Birren, J Neurosci 17, 9573–82 (1997); H. S. Wang, D. McKinnon, J Physiol (Lond) 485, 319–35 (1995).
8. L. Paquet, B. Massie, R. E. Mains, J. Neurosci 16, 964–73 (1996).
9. Seven non-infected cells were compared to seven cells infected with AdEGI and AdVgRXR (data not shown).
10. H. S. Wang, D. McKinnon, J. Physiol (Lond) 492, 467–78 (1996).
11. This effect was not statistically significant (p=0.14).
12. The effects of different levels of expression of the Kir2.1 protein were probed by comparing cells infected either with the polycistronic construct (AdEGI-Kir2.1) or the fusion construct (AdEG-Kir2.1), which produced different levels of GFP fluorescene and current density.
13. P. Rakic, H. Komuro, J Neurobiol 26, 299–315 (1995); S. B. Kater, L. R. Mills, J. Neurosci 11, 891–9 (1991).
14. C. G. Wasterlain, Y. Shirasaka, A. M. Mazarati, I. Spigelman, Epilepsy Res 26, 255–65 (1996).
15. A. Dray & H. Rang, Trends in Neurosci. 21 315–317 (1998).

We claim:

1. A method of altering cellular excitability, comprising the step of:
   delivering a genetic construct to a mammalians somatic cell, said genetic construct comprising an inducible promoter and a sequence encoding an ion channel, wherein the inducible promoter regulates transcription of the sequence, wherein the inducible promoter is regulated by an externally controllable stimulus, whereby the excitability of the cell is regulated by the externally controllable stimulus.

2. The method of claim 1 wherein the ion channel is voltage gated.

3. The method of claim 1 wherein the ion channel is ligand gated.

4. The method of claim 1 wherein the ion channel is inwardly rectifying.

5. The method of claim 1 wherein the ion channel is a potassium channel.

6. The method of claim 1 wherein the ion channel is neurotransmitter gated.

7. The method of claim 1 wherein the cell is a neuron.

8. The method of claim 1 wherein the cell is a muscle cell.

9. The method of claim 1 wherein the cell is an endocrine cell.

10. The method of claim 1 wherein the cell is a cancer cell.

11. The method of claim 1 wherein the inducible promoter is regulated by a hormone.

12. The method of claim 1 wherein the inducible promoter is regulated by a hormone analogue.

13. The method of claim 1 wherein the inducible promoter is regulated by an antibiotic.

14. The method of claim 1 wherein the inducible promoter is regulated by heat shock.

15. The method of claim 1 wherein the inducible promoter is regulated by a heavy metal ion.

16. The method of claim 1 wherein the inducible promoter is regulated by a cytokine.

17. The method of claim 1 wherein the inducible promoter is regulated by an interferon.

18. The method of claim 1 wherein the inducible promoter is regulated by a lactose operon inducer.

19. The method of claim 1 wherein the genetic construct is part of a viral vector.

20. The method of claim 1 wherein the delivery is to a muscle.

21. The method of claim 1 wherein the genetic construct is delivered as free DNA.

22. The method of claim 1 wherein the genetic construct is delivered in a liposome.

23. The method of claim 1 wherein the genetic construct is delivered by particle bombardment.

24. The method of claim 1 wherein the cell contains excitable membranes.

25. The method of claim 8 wherein the cell is a cardiac muscle cell.

26. The method of claim 8 wherein the cell is a skeletal muscle cell.

27. The method of claim 8 wherein the cell is a smooth muscle cell.

28. The method of claim 13 wherein the inducible promoter is regulated by tetracycline.

29. The method of claim 22 wherein the inducible promoter is regulated by isopropyl-B-D-thiogalactoside (IPTG).

30. The method of claim 18 wherein the inducible promoter is regulated by lactose.

31. The method of claim 19 wherein the genetic construct is part of an adenovirus vector.

32. The method of claim 19 wherein the genetic construct is part of an adeno-associated viral vector.

33. The method of claim 19 wherein the genetic construct is part of a herpes virus vector.

34. The method of claim 19 wherein the genetic construct is part of a retrovirus vector.

35. The method of claim 34 wherein the genetic construct is part of a lentivirus vector.

36. A method of altering cellular excitability, comprising the step of:

delivering a genetic construct to a mammalian neuronal cell, said genetic construct comprising an ecdysone-inducible promoter and a sequence encoding a potassium ion channel, wherein the inducible promoter regulates transcription of the sequence, wherein the inducible promoter is regulated by muristerone A, whereby the excitability of the cell is regulated by muristerone A.

37. A genetic construct for delivery to a mammalian neuronal cell, said genetic construct comprising:

a sequence encoding a potassium ion channel which is inwardly rectifying; and an ecdysone-inducible promoter;

wherein the ecdysone-inducible promoter regulates transcription of the sequence, and wherein the ecdysone-inducible promoter is regulatable by muristerone A.

38. The genetic construct of claim 37 which is contained in an adenoviral vector.

* * * * *

UNITED STATES PATENT AND TRADEMARK OFFICE
CERTIFICATE OF CORRECTION

PATENT NO. : 6,214,620 B1
DATED : April 10, 2001
INVENTOR(S) : David C. Johns et al.

It is certified that error appears in the above-identified patent and that said Letters Patent is hereby corrected as shown below:

Column 1,
Lines 6-9, please delete "This invention was made using funding supplied by the U.S. National Institutes of Health. Under the terms of NIH grant DA-00266, the U.S. government retains certain rights in the invention."

Column 10, claim 1,
Line 50, "mammalians" has been replaced with -- mammalian, --.

Column 12, claim 29,
Line 3, "22" has been replaced with -- 18 --,
Line 4, "isopropyl-B-D-thiogalactoside" has been replaced with -- isopropyl-β-D-thiogalactoside --.

Signed and Sealed this

Eleventh Day of December, 2001

Attest:

NICHOLAS P. GODICI
Attesting Officer    Acting Director of the United States Patent and Trademark Office